(12) United States Patent
Dolgin (10) Patent No.: US 6,772,011 B2
(45) Date of Patent: Aug. 3, 2004

(54) TRANSMISSION OF INFORMATION FROM AN IMPLANTED MEDICAL DEVICE

(75) Inventor: Alexander Dolgin, Lexington, MA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 10/224,118

(22) Filed: Aug. 20, 2002

(65) Prior Publication Data

US 2004/0039423 A1 Feb. 26, 2004

(51) Int. Cl.$^7$ ................................................. A61N 1/08
(52) U.S. Cl. ........................................ 607/61; 607/60
(58) Field of Search .................................... 607/30–61

(56) References Cited

U.S. PATENT DOCUMENTS

| | | |
|---|---|---|
| 4,665,896 A | 5/1987 | LaForge et al. |
| 5,630,836 A | 5/1997 | Prem et al. |
| 5,755,748 A | 5/1998 | Borza |
| 5,876,425 A | 3/1999 | Gord et al. |
| 5,948,006 A | 9/1999 | Mann |
| 6,327,504 B1 | 12/2001 | Dolgin et al. |
| 6,442,434 B1 * | 8/2002 | Zarinetchi et al. |

* cited by examiner

Primary Examiner—Scott M. Getzow
(74) Attorney, Agent, or Firm—Fish & Richardson P.C., P.A.

(57) ABSTRACT

An implanted medical apparatus and external power source use the same coils for energy transfer to the implanted medical device as used for transmission of control signals from the implanted device. In one example, implanted circuitry generates a feedback control signal indicative of the load voltage level of a load-generating medical device and superimposes the feedback signal on an inductor capacitor (LC) tank circuit for detection by the external powering apparatus. The external powering apparatus uses the feedback signal to control the energy transfer to the implanted medical device, thus regulating the load voltage at the load-generating medical device. The feedback control signal may be a sequence of pulses whose frequency indicates the load voltage level. Other information besides load voltage level may also be transmitted from the implanted device, such as telemetry and logic information.

43 Claims, 4 Drawing Sheets

TRANSMISSION OF INFORMATION FROM AN IMPLANTED MEDICAL DEVICE

TECHNICAL FIELD

This invention relates to devices that require the transfer of energy from a power source apparatus outside the body to an implanted medical device apparatus located inside the body, and more particularly to the transmission of information from the implanted apparatus to the power source apparatus, for example, to regulate the power supplied by the power source apparatus.

BACKGROUND

A transcutaneous energy transfer system (TETS) provides a means of transferring electrical energy from an external power supply apparatus to an implanted medical device through the skin of the patient. In a typical TETS, energy is transferred by magnetically coupling an external coil, located in the external power supply apparatus, to an internal coil associated with the implanted medical device.

Implanted devices receiving power from an external source typically require a load voltage within a specified operating range. An implanted blood pump may require, for example, a load voltage of not less than twelve volts, but no more than fifteen volts. The external power supply apparatus therefore needs to deliver the appropriate amount of energy to the implanted device so that the load voltage remains within the specified operating range. The load voltage level at any given time is determined by the amount of energy being transferred from the external power supply apparatus, the efficiency of the magnetic coupling between the external and internal coils, and the load imposed by the implanted medical device. The positioning of the external coil relative to the internal coil affects the efficiency of the magnetic coupling, and if the magnetic coupling is less than optimal, the external power supply apparatus may need to transmit more energy to maintain the load voltage within the specified operating range. The magnetic coupling efficiency may also change over time because, for example, patient movement may result in a change in position of the external coil relative to the internal coil, or because of the presence of an electromagnetic signal interfering with the efficiency of the magnetic coupling. Of course, fluctuations in the operation of the implanted device occur, and thus the load imposed by the medical device typically will vary over time.

To regulate the load voltage level, a feedback signal indicating the present load voltage level may be communicated from the implanted apparatus to the external power supply apparatus. One known method of providing this feedback information involves the transmission of radio frequency (RF) signals from the implanted device to the external power supply apparatus, which requires RF transmitters and receivers. Another known method involves transmitting an infrared signal with the feedback information through the patient's skin. Yet another method is to add coils to the external apparatus and the implanted apparatus, in addition to the power transfer coils, to transmit the feedback signal from the implanted device to the external power supply apparatus.

In addition to feedback information being transmitted to regulate the load voltage level, other information may also be transmitted from an implanted medical device. For example, other information that may be transmitted may include telemetry or other logic information such as, in the case of a blood pump being the load-generating device, an indication that the pump is operating properly or is in fault, that an internal battery is fully charged or not, or whether the pump is operating on main or redundant components.

SUMMARY

The invention, in one general aspect, features a medical TETS that provides feedback information from an implanted medical device to an external power source using the same coils over which power is transferred from the external power source to the implanted medical device.

In an aspect, an implantable device that requires electrical power from an external power source for operation has an inductor-capacitor (LC) tank circuit that receives power from the external source and delivers the power to a load-generating device. Feedback circuitry senses a load voltage level of the power delivered to the load-generating device and produces a feedback signal indicative of the load voltage level. The feedback signal is superimposed on the LC tank circuit for communication to the external power source.

The feedback signal, in one implementation, comprises a series of pulses at varying frequencies indicative of the load voltage level. The pulses may be generated at varying frequencies within a specified range with a center frequency, for example, one kilohertz. The center frequency may indicate that the load voltage level is the desired level and no adjustment needs to be made to the amount of power the external power source is delivering, while frequencies above and below the center frequency may indicate that the amount of power the external power source is delivering needs to be adjusted to bring the load voltage level back to the desired level.

The feedback circuitry may have a voltage-to-frequency converter. The voltage-to-frequency converter may include an error amplifier that compares the load voltage level to a reference voltage and generates a difference signal, and a controller to receive the difference signal and generate the feedback signal. The feedback circuitry may also have a switch that receives the feedback signal, and that is coupled with the LC tank circuit so that during the time the feedback signal is pulsed high the switch closes and the LC tank circuit is short-circuited to superimpose the feedback signal on the LC tank circuit.

The implanted medical device may also include a rectifier that includes first and second diodes having a forward bias directed toward a positive terminal of the load-generating device. The first diode may be coupled to a first terminal of the LC tank circuit and the second diode coupled to a second terminal of the LC tank circuit. The rectifier may also have first and second transistor switches whose current conducting terminals are coupled, respectively, between the first terminal of the LC tank circuit and negative terminal of the load-generating device and between the second terminal of the LC tank circuit and the negative terminal of the load-generating device. The first and second transistor switches may serve as the switch, each receiving the feedback signal at their gates and being activated by pulses in the feedback signal.

In another aspect, the invention features an external power source for an implantable device. An electrical power source is provided. A pulse-width modulator and driver generates a power signal that is transmitted over an LC tank circuit. A sensor senses a feedback signal indicative of a load voltage level that is provided by the implantable device through the LC tank circuit. The external power source varies the amount of power delivered to the implantable device in response to the feedback signal.

The external power source may also include a decoder that receives the sensed feedback signal, determines the frequency of the pulses in the feedback signal, and generates a voltage signal indicative of the frequency of the pulses in the feedback signal. The feedback signal sensed by the external power source may, as discussed previously, comprise a series of pulses, the frequency that the pulses are generated being indicative of the load voltage level. The power signal may be a rectangular pulse whose duty cycle varies the amount of energy transferred to the implantable device. The frequency range of the feedback signal may differ from the frequency of the power signal so that in the external power source, the power signal may be filtered to extract the feedback signal. The external power source may also include a tuning circuit that monitors a voltage component and a current component of the power signal so that the signal components have an ideal timing relationship.

In another embodiment, the external power source may also include a circuit that senses the rate of change of current through the primary coil. In this embodiment, the feedback signal includes, in addition to a pulsed feedback signal of the type described previously, another signal that is indicative of the rate of change of current through the LC tank circuit. The circuit that senses the rate of change of current through the coil may be a resistor-capacitor (R-C) circuit that receives a current through it that is indicative of the current through the coil. The R-C circuit has a capacitor with a voltage thereon indicative of the rate of change of current through the coil.

In a further aspect, the invention features a medical system with transcutaneous energy transfer. The medical system includes an external power source having a power driver and an LC tank circuit primary coil. An implantable device requires electrical power from an external power source for operation. The implantable device also includes an LC tank circuit that receives power from the external power source, and a load-generating device to which the received power is delivered. Feedback circuitry in the implantable device senses a load voltage level of the power delivered to the load-generating device, produces a feedback signal indicative of the load voltage level, and superimposes the feedback signal on the implantable device's LC tank circuit for communication to the external power source.

The external power source of the medical system may include a sensor that senses the feedback signal communicated from the implantable device. The external power source may also include a decoder that receives the feedback signal sensed by the sensor, determines the frequency of the pulses in the feedback signal, and generates a voltage signal indicative of the frequency of the pulses. A pulse-width modulator and driver that receive the voltage signal and generate a power signal transferring a desired amount of energy to the implantable device may also be included. The external power source may also include a tuning circuit that monitors a voltage componet and a current component of the power signal so that the signal components have an ideal timing relationship.

The feedback signal may comprise a series of pulses, the frequency that the pulses are generated being indicative of the load voltage level. The power signal may be a rectangular pulse whose duty cycle varies the amount of energy transferred to the implanted device. The frequency range of the feedback signal may differ from the frequency of the power signal so that in the external power source, the power signal may be filtered to extract the feedback signal. The medical system may include feedback circuitry including an error amplifier that receives the load voltage level, compares the load voltage level to reference voltage, and generates a difference signal indicative of the load voltage level. A controller that receives the difference signal and generates the feedback signal may also be included.

The implantable device of the medical system may further include feedback circuitry comprising a switch that receives the feedback signal and is coupled to the implantable device's LC tank circuit so that during the time the feedback signal is pulsed high the switch closes and the LC tank circuit is short-circuited to superimpose the feedback signal on the LC tank circuit. The implantable device may further comprise a rectifier that includes first and second diodes having a forward bias directed toward a positive terminal of the load-generating device. The first diode may be coupled to a first terminal of the LC tank circuit and the second diode coupled to a second terminal of the LC tank circuit. The rectifier may also have first and second transistor switches whose current conducting terminals are coupled, respectively, between the first terminal of the LC tank circuit and negative terminal of the load-generating device and between the second terminal of the LC tank circuit and the negative terminal of the load-generating device. The first and second transistor switches may serve as the switch, each receiving the feedback signal at their gates and being activated by pulses in the feedback signal.

In another aspect, the invention provides an implantable device requiring electrical power from an external power source for operation. The implantable device has an LC tank circuit that receives power from the external power source, and a load-generating device to which the received power is delivered. Circuitry in the implantable device senses a condition, produces a signal indicative of the condition, and superimposes the signal on the LC tank circuit for communication to the external power source.

In various embodiments, the signal being superimposed on the LC tank circuit may be one or more pulses. The load-generating device may be, for example, a blood pump, in which case the condition being sensed may be whether the blood pump is in an operating state or a fault state, whether the blood pump is operating on primary components or redundant components. In the example of a blood pump or other examples, the condition being sensed may be a charge condition for an internal battery. The signal-producing circuitry in the implantable device may include, as was the case with the feedback of load voltage information, a switch that receives the signal and is coupled with the LC tank circuit so that during the time the signal is pulsed high the switch closes and the coil is short-circuited to superimpose the signal on the LC tank circuit. The implantable device may also include the previously described circuitry that performs both rectifier and switch functions.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
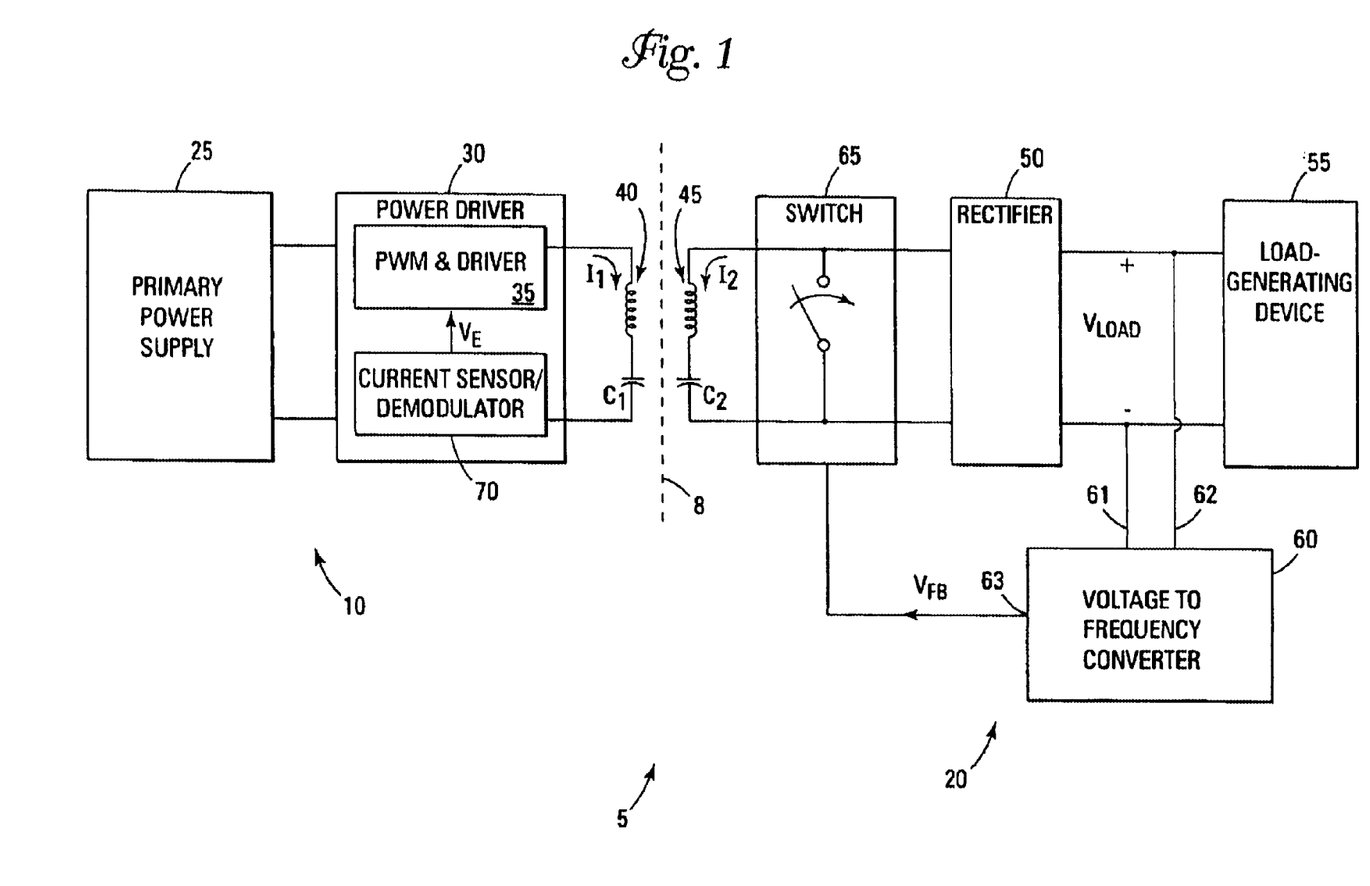
FIG. 1 is a block diagram of an embodiment of a medical system in accordance with the invention.

A medical system 5 in accordance with the invention, shown in FIG. 1, includes an external power supply apparatus 10 that supplies power to an implanted apparatus 20, and specifically to a load-generating device 55, such as a blood pump, which is part of the implanted apparatus 20. The external apparatus 10 has a primary coil 40 that may be positioned adjacent to a secondary coil 45 in the implanted apparatus 20 so that energy transfer occurs transcutaneously through the patient's skin 8. The implanted apparatus 20 provides a feedback signal to the external apparatus 10 via the same secondary coil 45 and primary coil 40 over which energy transfer to the implanted apparatus 20 occurs. The external apparatus 10 uses the feedback signal to control the amount of energy transferred to the implanted apparatus 20 and thus regulate the load voltage ($V_{LOAD}$) at device 55. This control accommodates, for example, load variations with device 55 and changes in energy transfer efficiency caused by changes in the efficiency of the magnetic coupling between the primary coil 40 and the secondary coil 45.

The external apparatus 10 includes a primary power supply 25. The power supply 25 may include a DC battery to produce the DC signal, may receive an AC signal from a power line and rectify the signal to produce the DC signal, or may have both a DC battery and the capability of receiving an AC signal from a power line. The power supply 25 in one implementation provides a DC signal to a power driver 30, as is conventional. In this implementation, power driver 30 contains a conventional pulse-width modulator (PWM) and driver 35 that conventionally produces a power signal having an output voltage with a variable duty cycle and fixed frequency, for example 160 kilohertz. The duty cycle of the power signal's output voltage is dictated by an error signal $V_E$, which will be described later.

The power signal has a current $I_1$ that flows through primary coil 40 and capacitor C1. The primary coil 40 and capacitor C1 form a conventional LC tank circuit. The LC tank circuit is a resonant circuit whose resonant frequency is set by the inductance of the primary coil 40 and the capacitance of the capacitor C1. In an example where the resonant frequency of the LC tank circuit is equal to the frequency of the power signal, current $I_1$ is generally in the shape of a sine wave.

Primary coil 40 is positioned next to the patient's skin 8 and aligned with the secondary coil 45 located just under the patient's skin 8 so that the primary coil 40 and the secondary coil 45 become magnetically coupled. The time-varying current $I_1$ flowing through the primary coil 40 induces a corresponding time-varying current $I_2$ that flows through the secondary coil 45 and capacitor C2. The secondary coil 45 and capacitor C2 form an LC tank circuit similar to the primary coil 40 and the capacitor C1 on the external apparatus 10. A rectifier 50 receives current $I_2$ when normally open switch 65 is open and provides a DC source of power for the load-generating device 55.

To regulate the load voltage ($V_{LOAD}$) at the load-generating device 55, the implanted apparatus 20 communicates a feedback signal back to the external apparatus 10 indicating the level of $V_{LOAD}$. As discussed previously, $V_{LOAD}$ may fluctuate or drop, for example, when device 55 is drawing more current, or when the positioning of primary coil 40 relative to the secondary coil 45 changes slightly thus causing a change in coupling efficiency. A voltage-to-frequency (V-F) converter 60 has two inputs 61 and 62 connected across $V_{LOAD}$ to monitor the level of $V_{LOAD}$. The V-F converter 60 produces, at its output 63, a feedback signal ($V_{FB}$) indicative of the level of $V_{LOAD}$.

In this implementation, the feedback signal $V_{FB}$ is a stream of brief pulses, the frequency of which varies with variations in $V_{LOAD}$. For example, a higher $V_{LOAD}$ level may result in the stream of pulses in the feedback signal $V_{FB}$ being generated at a lower frequency, whereas a lower $V_{LOAD}$ results in the stream of pulses in the feedback signal $V_{FB}$ being generated at a higher frequency. The frequency of pulses in the feedback signal $V_{FB}$ may be centered on a specific center frequency, such as one kilohertz in one implementation, which indicates no adjustment to the load voltage $V_{LOAD}$ is necessary. The frequency of pulses may range, for example, from 0.8 kilohertz to 1.3 kilohertz. The range of frequencies will typically be lower than the frequency of time-varying currents $I_1$ and $I_2$ flowing through coils 40 and 45, for reasons that will become apparent later.

The V-F converter 60 provides the feedback signal $V_{FB}$ to the normally open switch 65. Each pulse of the feedback signal $V_{FB}$ causes the switch 65 to close for the duration of the pulse. Closing the switch 65 thus short-circuits the LC tank circuit of secondary coil 45 and capacitor C1, or in other words, the end nodes of the series combination of secondary coil 45 and capacitor C2 are connected to a common node. This short-circuiting of the LC tank circuit causes a pulse in current $I_2$ to be generated across the secondary coil 45. Because of the coupling between coils 45 and 40, the current $I_1$ in the primary coil 40 is related to the voltage in the secondary coil 45. Reducing the voltage in the secondary coil 45 by shorting the LC tank circuit causes the current $I_1$ in the primary coil to reduce. Thus, the pulse generated in the secondary coil 45 induces a corresponding pulse in current $I_1$ across the primary coil 40. As such, the feedback information contained in the feedback signal $V_{FB}$ is transferred from the implanted apparatus 20 to the external apparatus 10 over the same coils 40 and 45 over which power is transferred from the external apparatus 10 to the implanted apparatus 20.

In the external apparatus 10, current sensor/demodulator 70 senses the current $I_1$ in the primary coil 40. Current $I_1$ contains two components: 1) the power signal produced by the PWM and driver 35, and 2) the feedback pulses caused by the closing of switch 65 in response to the feedback signal $V_{FB}$. The current sensor/demodulator 70 extracts the feedback pulses from the current $I_1$. The current sensor/demodulator 70 also processes the feedback pulses and generates an error signal $V_E$ that is provided to the PWM and driver 35. The error signal $V_E$ may be a signal whose voltage level goes lower as the load voltage $V_{LOAD}$ needs to be reduced, and goes higher as the load voltage $V_{LOAD}$ needs to be increased. Based on the error signal $V_E$, the PWM and driver 35 changes the duty cycle of the power signal it produces, thus altering the amount of energy transferred to the implanted apparatus 20. For example, if the error signal $V_E$ indicates that $V_{LOAD}$ is too low, the duty cycle of the power signal generated by the PWM and driver 35 is increased to increase the amount of energy transfer and thus raise the level of $V_{LOAD}$. Conversely, if $V_{LOAD}$ is too high, the duty cycle of the power signal is decreased to lower the level of $V_{LOAD}$. By changing the duty cycle of the power signal produced by PWM and driver 35, $V_{LOAD}$ is adjusted to remain within a specified operating range.

Figure 2:
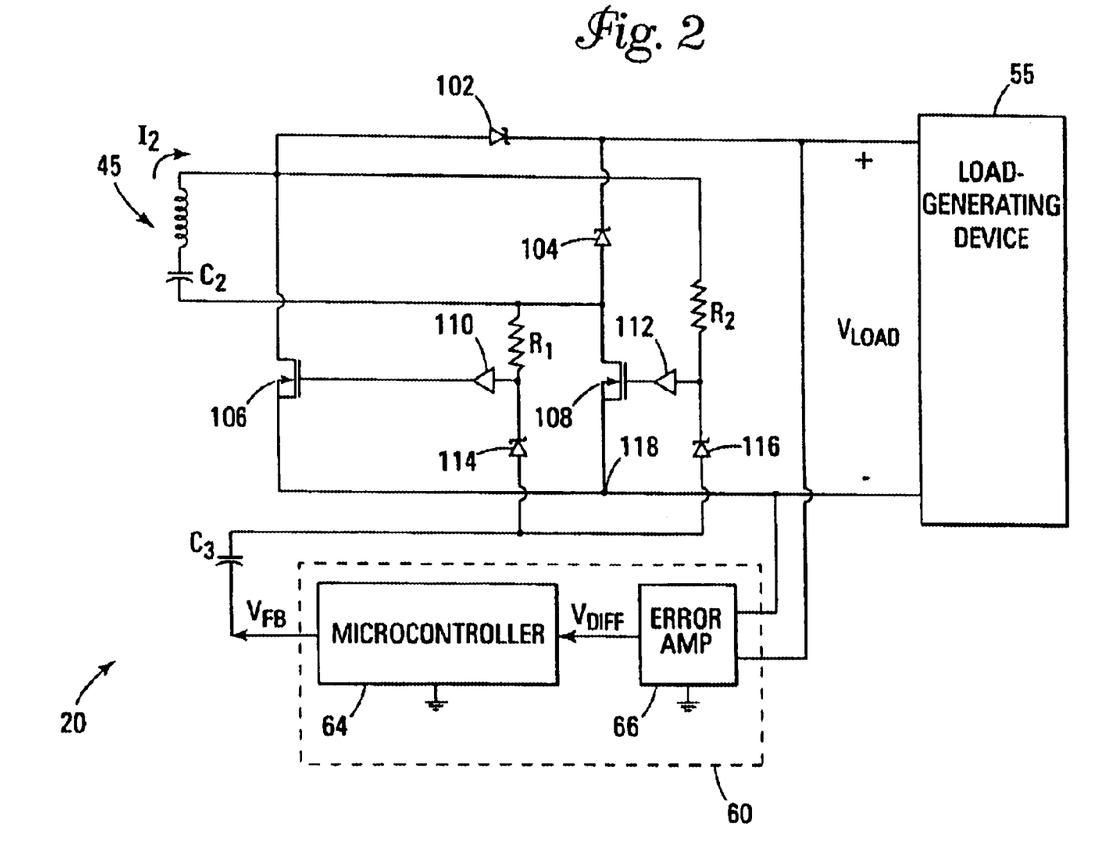
FIG. 2 is a diagram, partially a block diagram and partially a schematic diagram, of an embodiment of an implantable apparatus that may be used in the medical system shown in FIG. 1.

FIG. 2 shows details of an embodiment of the implanted apparatus 20 shown in FIG. 1. The function of the rectifier 50 shown in FIG. 1 is performed, in FIG. 2, by Zener diodes 102 and 104 and metal-oxide semiconductor field-effect transistors (MOSFETs) 106 and 108. When the coil current $I_2$ is positive, for example, current flows through diode 102 to the positive terminal (+) of the load-generating device 55, but does not flow to the negative terminal (−) because MOSFET 106 is off. The current return path from the negative terminal (−) is through MOSFET 108, which is possible because the positive coil current $I_2$ raises the level of voltage at an input to driver 112 to MOSFET 108, and thus MOSFET 108 is on. When current $I_2$ is negative, current flows through diode 104 to the positive terminal (+), but not to the negative terminal (−) because MOSFET 108 is off. The current return path from the negative terminal (−) is through MOSFET 106, which is possible because the negative coil current $I_2$ raises the level of voltage at an input to driver 110 to MOSFET 106, and thus MOSFET 106 is on. As such, the time-varying current $I_2$ is rectified to produce a DC power source to the medical device 55.

To monitor the load voltage $V_{LOAD}$, the V-F converter 60 in this implementation includes a conventional error amplifier 66. The error amplifier 66 measures the difference between $V_{LOAD}$ and a reference voltage, and provides, to a programmed microcontroller 64, a difference signal $V_{DIFF}$ corresponding to the difference between $V_{LOAD}$ and the reference voltage. In an example where load-generating device 55 has a target $V_{LOAD}$ of fourteen volts, the difference signal $V_{DIFF}$, after being scaled and shifted, may range from zero volts, for a low $V_{LOAD}$ such as ten volts, to five volts, for a high $V_{LOAD}$ such as twenty volts. The microcontroller 64 is programmed to process the received difference signal $V_{DIFF}$, which contains information regarding the present level of the load voltage $V_{LOAD}$, and in response generate the previously described pulsed feedback signal $V_{FB}$, which also contains information regarding the present level of the load voltage $V_{LOAD}$.

In FIG. 2, MOSFETs 106 and 108 operate as switches and thereby perform the function of the switch 65 shown in FIG. 1. The feedback signal $V_{FB}$ is provided to drivers 110 and 112 via capacitor C3 and diode 114 (for driver 110), and diode 116 (for driver 112). Capacitor C3 eliminates the DC component of $V_{FB}$ and passes only the pulse signal. The diodes 114 and 116 allow $V_{FB}$ to turn on the drivers 110 and 112, but prevent $V_{FB}$ from turning the drivers 110 and 112 off. Resistors R1 and R2 limit the voltage to drivers 110 and 112 while allowing $V_{FB}$ to override these voltages.

The drivers 110 and 112 drive, respectively, MOSFETs 106 and 108. Drivers 110 and 112 simultaneously turn on when feedback signal $V_{FB}$ pulses high, which simultaneously turns on MOSFETs 106 and 108. Simultaneously turning on MOSFETs 106 and 108 short-circuits the LC tank circuit of the secondary coil 45 and capacitor C1 for the duration that the feedback signal $V_{FB}$ pulses high. In other words, the end nodes of the series combination of coil 45 and capacitor C2 are both tied to common node 118. As mentioned previously, the shorting of the secondary coil 45 causes pulses in the current $I_2$, which in turn induces current pulses in the current $I_1$ through the primary coil 40. As a result, the feedback signal $V_{FB}$ is transferred from the internal apparatus 20 to external apparatus 10 using the same primary coil 40 and secondary coil 45 over which power is transferred from the external apparatus 10 to the internal apparatus 20.

As will be appreciated in the FIG. 2 implementation, MOSFETs 106 and 108 serve a dual function, as part of the rectifier 50 and also as the switch 65 that imposes the feedback pulses on the coil 45. As such, the switch 65 is implemented in a manner that complements the functioning of the rectifier 50.

Figure 3:
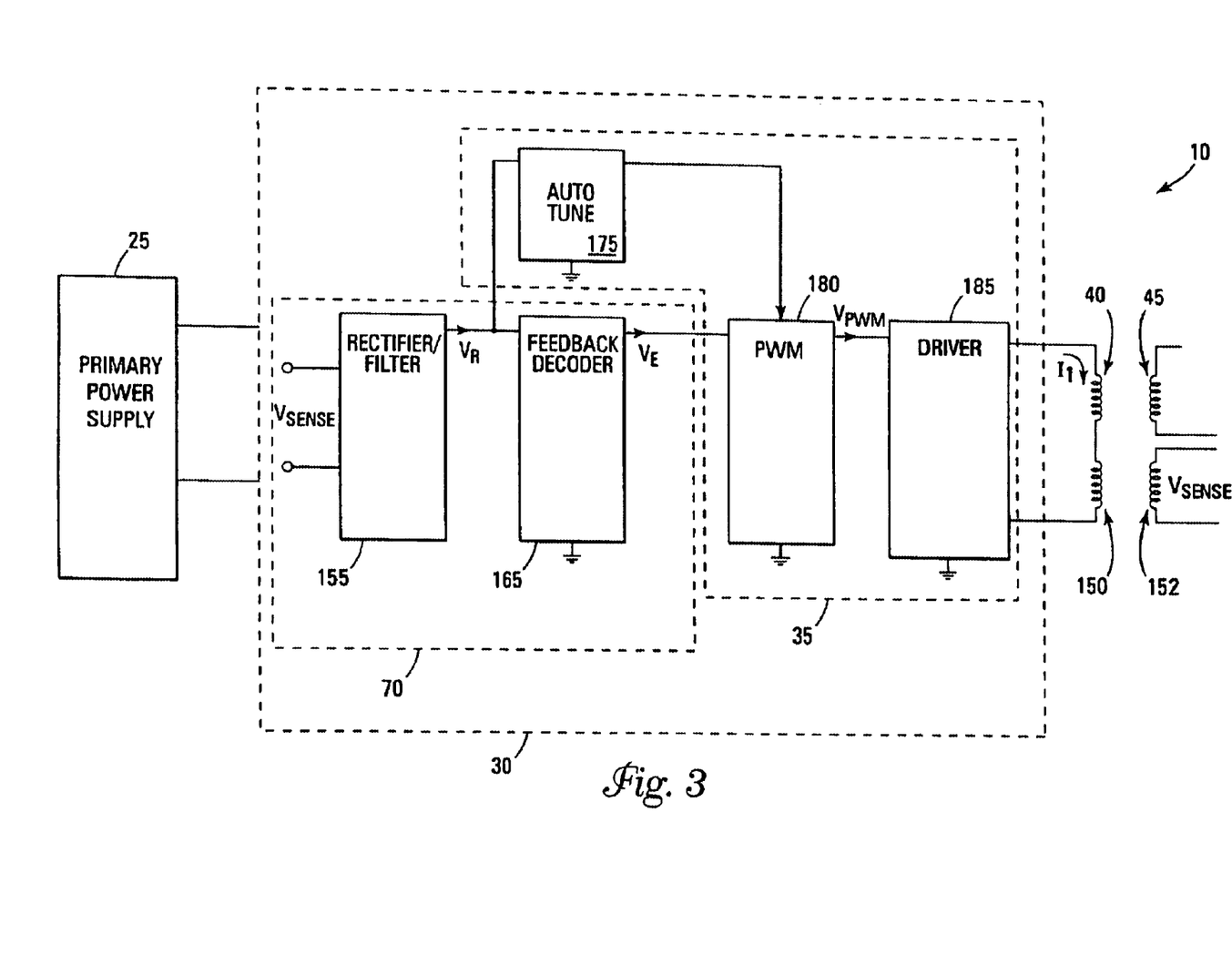
FIG. 3 is a block diagram of an embodiment of an external apparatus that may be used in the medical system shown in FIG. 1.

FIG. 3 shows details of an embodiment of the external apparatus 10 shown in FIG. 1. A conventional current-sensing coil 150 placed in series with the primary coil 40 senses the current $I_1$ flowing through the primary coil 40. The current $I_1$ passing through the current-sensing coil 150 induces a voltage signal ($V_{SENSE}$) proportional to the current $I_1$ on the secondary sensing coil 152. Like current $I_1$, the voltage signal $V_{SENSE}$ on the secondary sensing coil 152 contains two components: 1) the power signal produced by the PWM and driver 35, and 2) the feedback pulses.

The voltage signal $V_{SENSE}$ is received by a rectifier/filter 155. The rectifier/filter 155, firstly, rectifies the voltage signal $V_{SENSE}$, keeping only the positive portion of the signal. Second, the rectifier/filter 155 filters the power signal component from $V_{SENSE}$, leaving only the feedback signal component. This may be accomplished with a conventional low-pass filter, which may require the frequencies of the feedback signal to be much lower than the frequency of the power signal. For example, in one implementation the power signal has a frequency of 160 kilohertz and the feedback signal has a center frequency of one kilohertz. The resulting low frequency pulse signal $V_R$ thus reproduces in the external apparatus 10 the feedback signal $V_{FB}$ generated by the V-F converter 60 in the implanted apparatus 20.

The feedback decoder 165 receives the feedback signal $V_R$ from the rectifier/filter 155. Recall, the frequency of the feedback signal $V_{FB}$ is modulated with changes in the load voltage ($V_{LOAD}$) of the internal apparatus 20. The feedback decoder 165 demodulates the pulse signal $V_R$ creating an error signal $V_E$ whose voltage level corresponds to the frequency of the feedback signal pulses.

In one implementation, the feedback decoder 165 first amplifies and conditions the pulse signal $V_R$ received from the rectifier/filter 155. Next, a controller in the feedback decoder 165 receives the amplified and conditioned pulse signal $V_R$ and generates a constant-frequency, rectangular pulse signal whose duty cycle changes with respect to the frequency of the pulses in $V_R$. The rectangular pulse generated by the controller is then averaged by an integrator to produce the error signal $V_E$. The feedback decoder 165 supplies the averaged signal $V_E$ to the input of a PWM 180.

An auto tune circuit 175 monitors both the current signal and the voltage signal in the primary coil 40 to determine whether these signals have an ideal timing relationship with respect to each other. An ideal timing relationship may be necessary to prevent the undesirable dissipation of power in the external apparatus 10. For example, it may be ideal when the timing of the current signal in the primary coil 40 is slightly delayed with respect to the timing of the voltage signal.

In one implementation, the auto tune circuit 175 contains flip-flops that generate signals relating to the timing relationship between the voltage and current on primary coil 40. For example, a first flip-flop may generate a signal at the moment the current signal in the primary coil 40 changes polarity, i.e., the current signal crosses from negative to positive or from positive to negative. Similarly, a second flip-flop may generate a signal as the voltage signal in the primary coil 40 changes polarity. The output of these flip-flops may then be summed and compared to a fixed reference. If the voltage and current signals do not have an ideal timing relationship, the comparator may generate a tuning signal to be received by the PWM 180. Upon receiving this tuning signal, the PWM 180 may adjust the frequency of the signal it produces thereby achieving an ideal timing relationship between the voltage and current signals in the primary coil 40.

The PWM 180 may be any conventional PWM known in the art, or later developed. In one implementation, the PWM 180 receives the error signal $V_E$ from the feedback decoder 165 and generates a rectangular pulse signal ($V_{PWM}$) which is sent to a PWM driver 185. The duty cycle of the PWM output signal $V_{PWM}$ varies according to $V_E$. By varying the duty cycle of the PWM 180 output signal ($V_{PWM}$), the external apparatus 10 controls the amount of energy transferred to the internal apparatus 20. In one example, a duty cycle for $V_{PWM}$ of 50% results in the highest drive current $I_1$ on the primary coil 40. If the error signal $V_E$ indicates that $V_{LOAD}$ is below an optimal level, the duty cycle of the signal generated by the PWM 180 may be adjusted up to 50%, thereby increasing the amount of energy being transferred to the internal apparatus 20. Similarly, if the error signal $V_E$ indicates that $V_{LOAD}$ is above an optimal level, the duty cycle of the signal generated by the PWM 180 may be decreased from 50% to zero. By continuously changing the duty cycle of the signal $V_{PWM}$ produced by the PWM 180, $V_{LOAD}$ may be adjusted to remain within a specified operating range.

The PWM driver 185 may be any conventional driver known in the art, or later developed. The driver 185 receives the output signal $V_{PWM}$ of the PWM 180 and boosts the level of the current in the output signal. The driver 185 applies the output signal to the LC tank circuit of primary coil 40 and capacitor C1.

In summary, when the load voltage $V_{LOAD}$ raises, the frequency of pulses in the pulsed feedback signal $V_{FB}$ is lowered. As such, the error voltage $V_E$ is lowered, which reduces the duty cycle of the PWM output signal $V_{PMW}$ and the energy being transferred to the implanted apparatus 20. Conversely, when the load voltage $V_{LOAD}$ lowers, the frequency of pulses in the pulsed feedback signal $V_{FB}$ is raised, as is the error voltage $V_E$. This raises the duty cycle of the PWM output signal $V_{PMW}$ and consequently the energy being transferred to the implanted apparatus 20. As such, the load voltage $V_{LOAD}$ may be maintained to be within a desired range.

Figure 4:
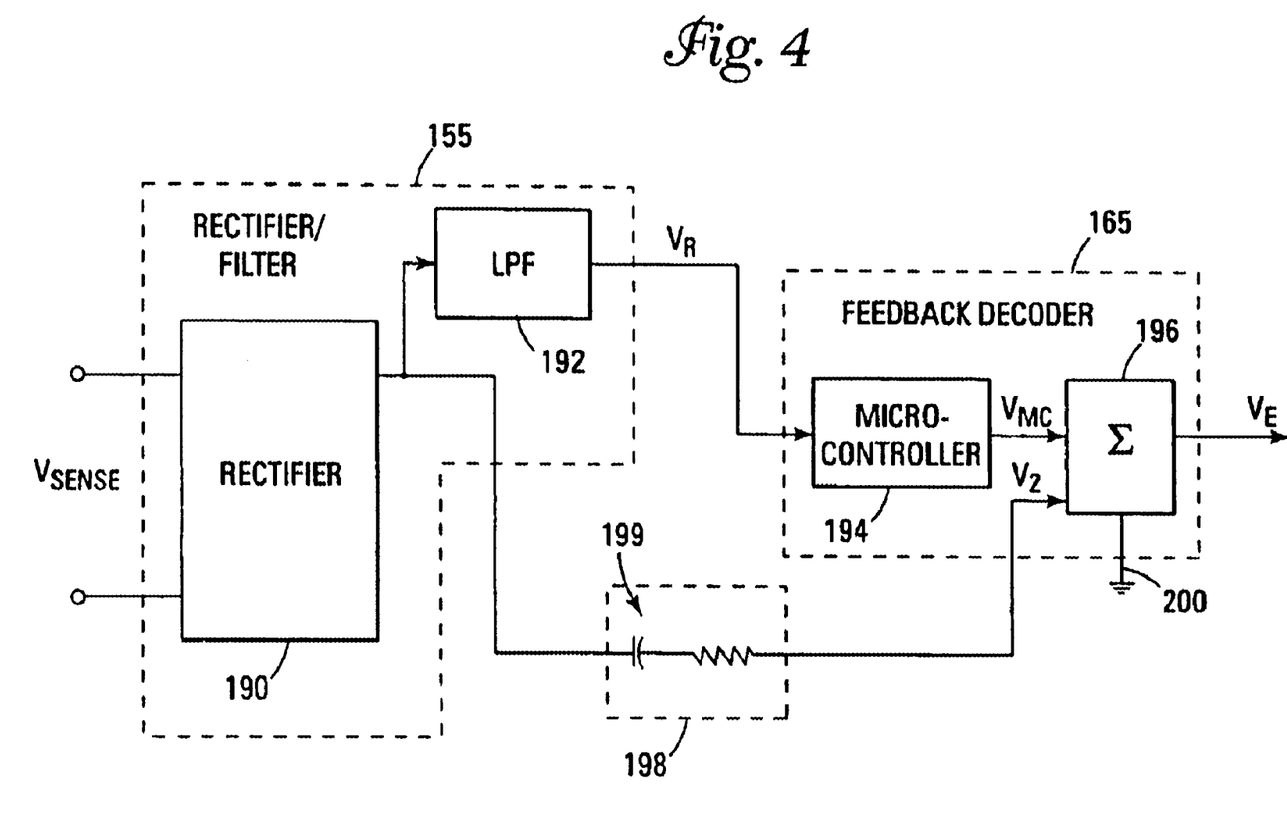
FIG. 4 is a diagram, partially a block diagram and partially a schematic diagram, of circuitry that may be used in various embodiments of the external apparatus of FIG. 3.

FIG. 4 shows example circuitry that may be included in an external power supply apparatus 10. The rectifier/filter 155 includes a rectifier 190 that receives the sensed voltage signal $V_{SENSE}$. The rectified sensed voltage signal is forwarded to a low pass filter 192, which, as discussed previously, eliminates the power signal component of the $V_{SENSE}$ signal. The filtered and rectified pulse signal $V_R$ is then forwarded to the feedback decoder 165, and in particular, a micro-controller 194 in the decoder 165. The micro-controller 194, in one implementation, is programmed to produce another pulsed signal $V_{MC}$ whose frequency is constant, but whose duty cycle corresponds to the frequency of pulses in the rectified and filtered pulsed signal $V_R$. In other words, when the frequency of pulses in the pulsed signal $V_R$ goes lower, the duty cycle of the signal $V_{MC}$ is reduced. The micro-controllers output signal $V_{MC}$ is sent to an integrator 196. The integrator 196, in one embodiment, averages the signal $V_{MC}$ over time and produces an output signal $V_E$ which has a voltage level that corresponds to the average voltage level of $V_{MC}$ received over a particular period of time. Thus, if the duty cycle of the signal $V_{MC}$ goes higher, then the error signal $V_E$ would likewise go higher.

In some cases, the responsiveness of the feedback system will be acceptable using only the information in the feedback signals (and thus only the microcontroller output signal $V_{MC}$). In other cases, more responsiveness may be desired. The current $I_1$ flowing through primary coil 40 is affected by load current going to device 55, coupling of coils 40 and 45, etc. As such, the magnitude of the primary current $I_1$ may not be trusted as a source of feedback information.

However, the rate of change in the primary current $I_1$ mirrors the rate of change of the load voltage $V_{LOAD}$. For example, with a faster increase of the load voltage $V_{LOAD}$, the primary current $I_1$ is increasing faster. As such, it is possible to use the differential of the primary current $I_1$ (that is, rate of change) as a contributing factor in the feedback control loop.

To achieve this higher responsiveness, a resistor-capacitor (R-C) circuit 198 may be added and connected to the output of rectifier 190 as shown in FIG. 4. The R-C circuit 198 receives the rectified voltage signal from rectifier 190, and the voltage $V_2$ gradually increases when the rate of change in primary current $I_1$ becomes greater.

In this implementation, the integrator 196 receives, in addition to the signal $V_{MC}$ from the micro-controller 194, another signal labeled $V_2$ from the R-C circuit 198. The integrator 196 adds both inputs $V_{MC}$ and $V_2$ and produces an error signal $V_E$ that takes into account both the frequency of feedback pulses in signal $V_R$ (and thus the duty cycle of $V_{MC}$) and the rate of change in $I_2$ that may be occurring. As such, the responsiveness of the feedback may be increased beyond what the frequency of feedback pulses would otherwise allow.

A number of embodiments of the invention have been described. For example, information other than load voltage $V_{LOAD}$ may be transmitted from an implanted apparatus to an external apparatus using pulses superimposed on the secondary coil 45 (see FIG. 2). For example, other information that may be transmitted may include telemetry or other logic information such as, in the case of a blood pump being the load-generating device, an indication that the pump is operating properly or is in fault, that an internal battery is fully charged or not, or whether the pump is operating on main or redundant components. Where information such as this is being transmitted, a coding scheme may be used so that different recognizable pulse sequences correspond to different conditions, and thus the external apparatus will be able to ascertain the condition being transmitted. The coding scheme may also include a pulse sequence that serves as a "start bit," to inform the external apparatus that the pulses that follow is condition information. A microcontroller or other circuitry may be included in the implantable apparatus (similar to the microcontroller 64 shown in FIG. 2), which receives information about sensed conditions, and produces the pulses corresponding to the conditions. Therefore, it will be understood that various modifications may be made without departing from the spirit and scope of the invention. Accordingly, other embodiments are within the scope of the following claims.

What is claimed is:

1. An implantable device requiring electrical power from an external power source for operation, comprising:
   an LC tank circuit that receives power from the external power source;
   a load-generating device to which the received power is delivered; and
   feedback circuitry that senses a load voltage level of the power delivered to the load-generating device, produces a pulsed feedback signal indicative of the bad voltage level, and superimposes the feedback signal on the LC tank circuit for communication to the external power source, wherein during a time that the feedback signal is superimposed on the LC tank circuit receipt of power from the external power source is interrupted.

2. The implantable device of claim 1 wherein the feedback signal comprises a series of pulses, the frequency that the pulses are generated being indicative of the load voltage level.

3. The implantable device of claim 2 wherein the feedback circuitry comprises:
   an error amplifier that receives the load voltage level, compares the load voltage level to a reference voltage, and generates a difference signal indicative of the bad voltage level; and
   a controller that receives the difference signal and generates the feedback signal.

4. The implantable device of claim 2 wherein the pulses are generated at varying frequencies within a specified range with a center frequency, and that center frequency indicates that the load voltage level is the desired level and no adjustment needs to be made to the amount of power the external power source is delivering, while frequencies above and below the center frequency indicate that the amount of power the external power source is delivering needs to be adjusted to bring to load voltage level back to the desired level.

5. The implantable device of claim 4 wherein the center frequency is about one kilohertz.

6. The implantable device of claim 4 wherein the frequency range of the feedback signal differs from the frequency of a power signal produced by the external power source so that in the external power source, the power signal may be filtered to extract the feedback signal.

7. The implantable device of claim 6 wherein the frequency tango of the feedback signal is less than the frequency of the power signal.

8. The implantable device of claim 2 wherein the feedback circuitry comprises a switch that receives the feedback signal and is coupled with the LC tank circuit so that during the time the feedback signal is pulsed high the switch closes and the LC tank circuit is short-circuited to superimpose the feedback signal on the LC tank circuit.

9. The implantable device of claim 8 farther comprising a rectifier that comprises:
   first and second diodes, to first diode being coupled to a first terminal of the LC tank circuit and the second diode being coupled to a second terminal of the LC tank circuit, and the first and second diodes both having a forward bias directed toward a positive terminal of the load-generating device; and
   first and second transistor switches whose current conducting terminals are coupled, respectively, between the first terminal of the LC tank circuit and the negative terminal of the load-generating device and between the second terminal of the LC tank circuit and the negative terminal of the load-generating device;
   wherein the first and second transistor switches serve as the switch and each receives the feedback signal at its gate, and the first and second transistor switches ate activated by the pulses in the feedback signal.

10. An implantable device requiring electrical power from an external power source for operation, comprising:
    an LC tank circuit that receives a power signal from the external power source; a rectifier that rectifies the power signal;
    a load-generating device to which the rectified power signal is delivered;
    a voltage-to-frequency converter that senses a load voltage level of the power delivered to the load-generating device and produces a pulsed feedback signal comprising a series of pulses, the frequency that the pulses are generated being indicative of tit load voltage level; and
    a switch that superimposes the pulsed feedback signal on the LC tank circuit for communication to the external power source.

11. The implantable device of claim 10 wherein the rectifier and the switch utilize common components.

12. The implantable device of claim 10 wherein the voltage-to-frequency converter comprises:
    an error amplifier that receives the load voltage level, compares the load voltage level to a reference voltage, and generates a difference signal indicative of the load voltage level; and
    a controller that receives the difference signal and generates the feedback signal.

13. The implantable device of claim 10 wherein the pulses are generated at varying frequencies within a specified range with a center frequency, and that center frequency indicates that the load voltage level is the desired level and no adjustment needs to be made to the amount of power the external power source is delivering, while frequencies above and below the center frequency indicate that the amount of power the external power source is delivering needs to be adjusted to bring the load voltage level back to the desired level.

14. The implantable device of claim 13 wherein the frequency range of the feedback signal differs from the frequency of the power signal so that in the external power source, the power signal may be filtered to extract the feedback signal.

15. The implantable device of claim 10 wherein the rectifier comprises:
    first and second diodes, the first diode being coupled to a first terminal of the LC tank circuit and the second diode being coupled to a second terminal of the LC tank circuit, and the first and second diodes both having a forward bias directed toward a positive terminal of the load-generating device; and
    first and second transistor switches whose current conducting terminals are coupled, respectively, between the first terminal of the LC tank circuit and the negative terminal of the load-generating device and between the second terminal of the LC tank circuit and the negative terminal of the load-generating device;
    wherein the first and second transistor switches serve as the switch and each receive the feedback signal at their gates, the first and second transistor switches being activated by the pulses in the feedback signal.

16. A medical system with transcutaneous energy transfer comprising:
    an external electrical power source having a power driver and a primary LC tank circuit; and
    an implantable device requiring electrical power from an external power source for operation, comprising:
    a secondary LG tank circuit that receives power from the external power source;
    a load-generating device to which the received power is delivered; and
    feedback circuitry that senses a load voltage level of the power delivered to the load-generating device, produces a pulsed feedback signal indicative of the load voltage level, and superimposes the feedback signal on the secondary LC tank circuit for communication to the external power source, wherein during a time that the feedback signal is superimposed on the LC tank circuit receipt of power from the external power source is interrupted.

17. The medical system of claim 6 wherein the feedback signal comprises a series of pulses, the frequency that the pulses are generated being indicative of the load voltage level.

18. The medical system of claim 7 wherein the power driver comprises: a sensor that senses the feedback signal communicated from the implantable device,
a decoder that receives the feedback signal sensed by the sensor, determines the frequency of the pulses in the feedback signal, and generates a voltage signal indicative of the frequency of the pulses; and
a pulse-width modulator and driver that receives the voltage signal and generates a power signal transferring a desired amount of energy to the implantable device.

19. The medical system of claim 18 wherein the power signal is a rectangular pulse whose duty cycle varies the amount of energy transferred to the implanted device.

20. The medical system of claim 19 wherein the frequency range of the feedback signal differs from the frequency of the power signal so that in to external power source, the power signal may be filtered to extract the feedback signal.

21. The medical system of claim 18 wherein the power driver further comprises a tuning circuit that monitors a voltage component and a current component of the power signal and times the power signal so that the signal components have an ideal timing relationship.

22. The medical system of claim 17 wherein the feedback circuitry comprises:
an error amplifier that receives the load voltage level, compares the load voltage level to a reference voltage, and generates a difference signal indicative of the load voltage level; and
a controller that receives the difference signal and generates the feedback signal.

23. The medical system of claim 17 wherein the feedback circuitry comprises a switch that receives the feedback signal and is coupled with the secondary LC tank circuit so that during the time the feedback signal is pulsed high the switch closes and the secondary LC tank circuit is short-circuited to superimpose the feedback signal on the secondary LC tank circuit.

24. The medical system of claim 23 further comprising a rectifier that comprises:
first and second diodes, the first diode being coupled to a first terminal of the secondary LC tank circuit and the second diode being coupled to a second terminal of the secondary LC tank circuit, and the first and second diodes both having a forward bias directed toward a positive terminal of the load-generating device; and
first and second transistor switches whose current conducting terminals are coupled, respectively, between the first terminal of the secondary LC tank circuit and the negative terminal of the load-generating device and between the second terminal of the secondary LC tank circuit and the negative terminal of the load-generating device;
wherein the first and second transistor switches serve as the switch and each receive the feedback signal at their gates, the first and second transistor switches being activated by the pulses in the feedback signal.

25. An external power source for an implantable device requiring electrical power from an external power source for operation, the external power source comprising:
an electrical power supply;
a pulse-width modulator and driver for generating a power signal;
an LC tank circuit for transmitting electrical energy; and
a sensor that senses a feedback signal provided by the implantable device through the LC tank circuit, the feedback signal indicative of a load voltage level and comprising a series of pulses, the frequency that the pulses are generated being indicative of the load voltage level;
wherein the external power source varies the amount of power delivered to the implantable device in response to the feedback signal.

26. external power source of claim 25 further comprising a decoder that receives the feedback signal sensed by the sensor, determines the frequency of the pulses in the feedback signal, and generates a voltage signal to be received by the pulsewidth modulator and driver that is indicative of the frequency of the pulses.

27. The external power source of claim 25 wherein the power signal is a rectangular pulse whose duty cycle varies the amount of energy transferred to the implanted device.

28. The external power source of claim 27 wherein the frequency range of the feedback signal differs from the frequency of the power signal so that the power signal maybe filtered to extract the feedback signal.

29. The external power source of claim 25 further comprising a tuning circuit that monitors a voltage component and a current component of the power signal and tunes the power signal so that the signal components have an ideal timing relationship.

30. The external power source of claim 25 further comprising a circuit that senses the rate of change of current through the LC tank circuit, and wherein the feedback signal further comprises a signal indicative of the rate of change of current though the LC tank circuit.

31. The external power source of claim 30 wherein the circuit that senses the rate of change of current through the LC tank circuit is an R-C circuit that receives a current therethrough indicative of the current through the LC tank circuit and that has a capacitor with a voltage thereon indicative of the rate of change of current through the LC tank circuit.

32. An implantable device requiring electrical power from an external power source for operation comprising:
an LC tank circuit that receives power from the external power source;
a load-generating device to which the received power is delivered; and
circuitry that senses a condition, produces a signal comprising one or more pulses and which is indicative of the condition, and superimposes the signal on the LC tank circuit for communication to die external power source.

33. The implantable device of claim 32 wherein the load generating device is a blood pump.

34. The implantable device of claim 33 wherein the condition being sensed is whether the blood pump is in an operating state or a fault state.

35. The implantable device of claim 33 wherein the condition being sensed is whether the blood pump is operating on primary components or redundant components.

36. The implantable device of claim 32 wherein the condition being sensed is a charge condition for an internal battery.

37. The implantable device of claim 32 wherein the circuitry comprises a switch that receives the signal and is coupled with the LC tank circuit so that during the time the signal is pulsed high the switch closes and the LC tank circuit is short-circuited to superimpose the signal on the LC tank circuit.

38. The implantable device of claim 32 further comprising a rectifier that comprises:
- first and second diodes, the first diode being coupled to a first terminal of the LC tank circuit and the second diode being coupled to a second terminal of the LC tank circuit and the first and second diodes both having a forward bias directed toward a positive terminal of the load-generating device; and
- first and second transistor switches whose current conducting terminals are coupled, respectively, between the first terminal of the LC tank circuit and the negative terminal of the load-generating device and between the second terminal of the LC tank circuit and the negative terminal of the load-generating device;
- wherein the first and second transistor switches serve as the switch and each receive the signal at their gates, the first and second transistor switches being activated by the pulses in the signal.

39. An implantable device requiring electrical power from an external power source for operation, comprising:
- an LC tank circuit that receives power from the external power source;
- a load-generating device to which the received power is delivered; and
- feedback circuitry that senses a load voltage level of the power delivered to the load generating device, produces a feedback signal indicative of the load voltage level, and superimposes the feedback signal on the LC rank circuit for communication to the external power source, wherein the feedback signal comprises a series of pulses and the frequency that the pulses are generated is indicative of the load voltage level.

40. The implantable device of claim 39 wherein the pulses are generated at varying frequencies within a specified range with a center frequency, and that center frequency indicates that the load voltage level is the desired level and no adjustment needs to be made to the amount of power the external power source is delivering, while frequencies above and below the center frequency indicate that the amount of power the external power source is delivering needs to be adjusted to bring the load voltage level back to the desired level.

41. The implantable device of claim 40 wherein the center frequency is about one kilohertz.

42. The implantable device of claim 39 wherein the frequency range of the feedback signal is less than the frequency of the power signal.

43. An implantable device requiring electrical power from an external power source for operation, comprising:
- an LC tank circuit that receives power from the external power source;
- a load-generating device to which the received power is delivered; and
- feedback circuitry that senses a load voltage level of the power delivered to the load-generating device, produces a feedback signal indicative of the load voltage level, and superimposes the feedback signal on the LC tank circuit the communication to the external power source, wherein the feedback circuitry comprises a switch that receives the feedback signal and is coupled with the LC tank circuit so that during the time the feedback signal is pulsed high the switch closes and the LC tank circuit is short-circuited to superimpose the feedback signal on the LC tank circuit.

\* \* \* \* \*

UNITED STATES PATENT AND TRADEMARK OFFICE
CERTIFICATE OF CORRECTION

PATENT NO.         : 6,772,011 B2
APPLICATION NO.    : 10/224118
DATED              : August 3, 2004
INVENTOR(S)        : Alexander Dolgin It is certified that error appears in the above-identified patent and that said Letters Patent is hereby corrected as shown below:

In the Claims:

In claim 7, column 11, line 37, delete "tango".

In claim 10, column 12, line 7, delete "tit" and insert --the--, therefor.

In claim 16, column 12, line 61, delete "LG" and insert --LC--, therefor.

Signed and Sealed this
Twenty-fifth Day of June, 2013

Teresa Stanek Rea
*Acting Director of the United States Patent and Trademark Office*